United States Patent
Sexton et al.

(10) Patent No.: US 9,428,630 B2
(45) Date of Patent: *Aug. 30, 2016

(54) WATER-IN-OIL POLYACRYLAMIDE-BASED MICROEMULSIONS AND RELATED METHODS

(71) Applicant: EXACTO, INC., Sharon, WI (US)

(72) Inventors: Franklin E. Sexton, Richmond, IL (US); Ryan T. Strash, Trevor, WI (US); Todd J. O'Connell, Wonder Lake, IL (US)

(73) Assignee: Exacto, Inc., Sharon, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/478,777

(22) Filed: Sep. 5, 2014

(65) Prior Publication Data
US 2014/0378554 A1 Dec. 25, 2014

Related U.S. Application Data

(63) Continuation-in-part of application No. 13/091,686, filed on Apr. 21, 2011, now Pat. No. 9,309,378, which is a continuation-in-part of application No. 12/487,710, filed on Jun. 19, 2009, now Pat. No. 9,307,758.

(51) Int. Cl.
*A01N 25/10* (2006.01)
*C09K 17/00* (2006.01)
*C08K 5/09* (2006.01)
(Continued)

(52) U.S. Cl.
CPC ............... *C08K 5/09* (2013.01); *A01N 25/04* (2013.01); *C08K 3/20* (2013.01); *C08K 5/06* (2013.01); *C08L 33/26* (2013.01); *C08L 71/02* (2013.01);

(58) Field of Classification Search
CPC .............................. A01N 25/04; A01N 25/30
USPC .................................................. 504/361, 360
See application file for complete search history.

(56) References Cited

U.S. PATENT DOCUMENTS 3,346,494 A 10/1967 Robbins et al.
3,624,019 A 11/1971 Anderson et al.
(Continued)

FOREIGN PATENT DOCUMENTS

CN 101933509 A 1/2011
KR 20000068408 A 11/2000
(Continued)

OTHER PUBLICATIONS

International Search Report, PCT/US2013/034468, Dec. 16, 2013, 3 pages.
(Continued)

*Primary Examiner* — David Karst
(74) *Attorney, Agent, or Firm* — Berenato & White, LLC

(57) ABSTRACT

A water-in-oil microemulsion, including a polyacrylamide, a fatty acid, a surfactant, an oil continuous phase, and an aqueous discontinuous phase in the oil continuous phase. The fatty acid includes a tall oil fatty acid, oleic acid, or a combination of a tall oil fatty acid and oleic acid. The water-in-oil microemulsion contains 6 to 48 parts by weight of the polyacrylamide, 30 to 62 parts by weight of the fatty acid, and 20 to 44 parts by weight of the surfactant per 100 parts by weight of the polyacrylamide, the fatty acid, and the surfactant combined.

20 Claims, 2 Drawing Sheets

Figure 1:
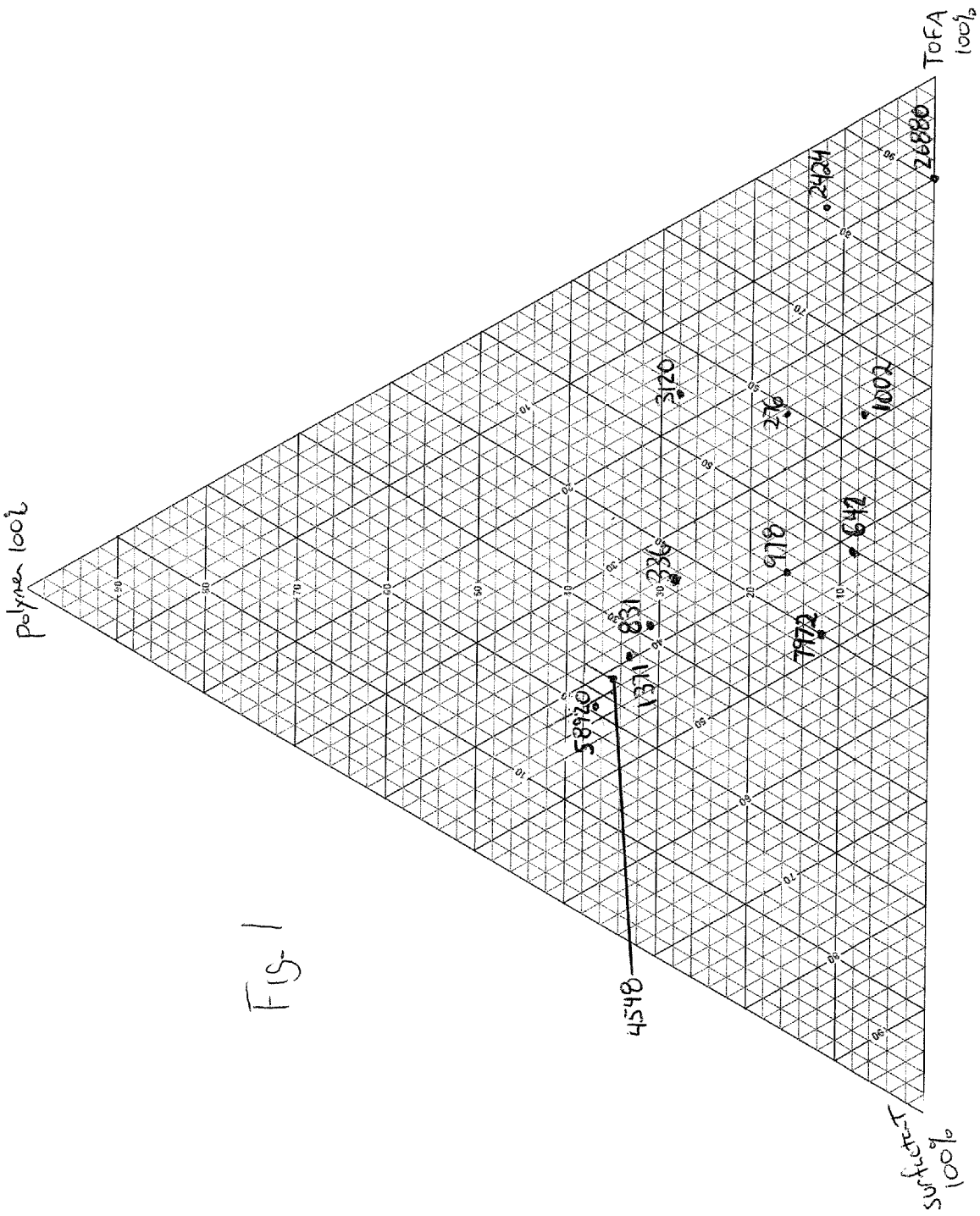

(51) Int. Cl.
*C08K 3/20* (2006.01)
*C08K 5/06* (2006.01)
*C08L 71/02* (2006.01)
*A01N 25/04* (2006.01)
*C08L 33/26* (2006.01)
*C08L 91/00* (2006.01)
*C08K 5/00* (2006.01)
*C08K 5/101* (2006.01)

(52) U.S. Cl.
CPC .............. *C08L 91/00* (2013.01); *C08K 5/0058* (2013.01); *C08K 5/101* (2013.01)

(56) References Cited

U.S. PATENT DOCUMENTS

| | | |
|---|---|---|
| 4,052,353 A | 10/1977 | Scanley |
| 4,413,087 A | 11/1983 | Bernot |
| 4,681,912 A | 7/1987 | Durand et al. |
| 4,696,962 A | 9/1987 | Danner et al. |
| 4,904,695 A | 2/1990 | Bell |
| 4,915,859 A | 4/1990 | Kerr et al. |
| 4,956,399 A | 9/1990 | Kozakiewicz et al. |
| 5,037,653 A | 8/1991 | Dawson |
| 5,037,654 A | 8/1991 | Puritch et al. |
| 5,292,800 A | 3/1994 | Moench et al. |
| 5,490,943 A | 2/1996 | Eicken et al. |
| 5,549,840 A | 8/1996 | Mondin et al. |
| 5,587,357 A | 12/1996 | Rhinesmith |
| 5,656,289 A | 8/1997 | Cho et al. |
| 5,763,530 A | 6/1998 | Chen et al. |
| 5,811,383 A | 9/1998 | Klier et al. |
| 5,952,398 A | 9/1999 | Dietz et al. |
| 6,025,432 A | 2/2000 | Ryan |
| 6,110,981 A | 8/2000 | Davies et al. |
| 6,143,830 A | 11/2000 | Utz et al. |
| 6,172,031 B1 | 1/2001 | Stevens |
| 6,326,013 B1 | 12/2001 | Lemann et al. |
| 6,410,605 B1 | 6/2002 | Shimada et al. |
| 6,475,974 B1 | 11/2002 | Leboucher et al. |
| 6,686,417 B1 | 2/2004 | Reekmans et al. |
| 6,709,716 B2 | 3/2004 | Uy et al. |
| 6,803,345 B2 | 10/2004 | Herold et al. |
| 6,835,761 B2 | 12/2004 | Harrison |
| 7,074,752 B2 | 7/2006 | Gordon |
| 2003/0147825 A1 | 8/2003 | Chiarelli et al. |
| 2004/0194658 A1 | 10/2004 | Konno et al. |
| 2005/0101510 A1 | 5/2005 | Mondin et al. |
| 2005/0118210 A1 | 6/2005 | Kachi et al. |
| 2005/0234166 A1 | 10/2005 | Lau |
| 2005/0239957 A1 | 10/2005 | Pillsbury et al. |
| 2006/0004130 A1 | 1/2006 | Strominger et al. |
| 2006/0289137 A1 | 12/2006 | Gelman et al. |
| 2007/0049496 A1 | 3/2007 | Messerschmidt et al. |
| 2007/0197418 A1 | 8/2007 | Rahse |
| 2007/0219315 A1 | 9/2007 | Braun |
| 2010/0037513 A1 | 2/2010 | Petrucci et al. |
| 2013/0231429 A1 | 9/2013 | Sexton et al. |
| 2014/0323312 A1 | 10/2014 | Sexton et al. |
| 2014/0323609 A1 | 10/2014 | Sexton et al. |

FOREIGN PATENT DOCUMENTS

| | | |
|---|---|---|
| WO | 8810274 A1 | 12/1988 |
| WO | 2005077336 A1 | 8/2005 |
| WO | 2014158175 A1 | 10/2014 |

OTHER PUBLICATIONS

Applied Polymer systems, Inc., APS 600 Series Silt Stop, Applied Polymer Systems, Inc., 2002, 2 pages, http://www.siltstop.com/silt_stop_aps_600.html.

Flick, E.W., Cosmetic Additives—An Industrial Guide, 1991, William Andrew Pubilshing/Noyes, p. 401, 412.

Lentz et al., "Field Results Using Polyacrylamide to Manage Furrow Erosion and Infiltration", Soil Science, Oct. 1994, vol. 158, Issue 4, Abstract http://journals.lww.com/soilsci/Abstract/1994/10000/FIELD_RESULTS_USING_POLYACRYLAMIDE_TO_MANAGE.7.aspx.

Polyacrylamide (PAM) Definition, pp. PM-1-PM-5. http://www.michigan.gov/documents/deg/nps-polyacrylamide_332130_7.pdf, 2010.

Flick, E.W., Industrial Surfactants, 1993, Noyles Publications, Second Edition, p. 240.

WATER-IN-OIL POLYACRYLAMIDE-BASED MICROEMULSIONS AND RELATED METHODS

CLAIM OF PRIORITY

This application is a continuation-in-part of U.S. patent application Ser. No. 13/091,686 filed on Apr. 21, 2011, which is a continuation-in-part of U.S. patent application Ser. No. 12/487,710 filed Jun. 19, 2009, the complete disclosures of which are incorporated herein by reference. This application is also related to U.S. patent application Ser. No. 14/036,214.

TECHNICAL FIELD

The present invention relates to polyacrylamide-based compositions, and more particularly, to polyacrylamide-based compositions as microemulsions.

BACKGROUND

Water-soluble polymers are long known to be very useful in both agricultural and industrial applications. Water-soluble linear polyacrylamides, for example, are useful because of their superior properties of high solubility and low use rates, among others. By far, the major use for linear polyacrylamides is in the treatment of water, especially wastewater.

In wastewater treatment and uses like canal sealing, polyacrylamide causes flocculation or agglomeration of fine particles. Flocculation, where relatively light particles are attracted together to form heavier particles, causes the particles to sink rather than float, clarifying the water. In agricultural sprays, the ability of these polymers to attract and retain water and add viscosity is utilized to enhance the effectiveness of the sprays, in addition to other purposes.

These linear polyacrylamides are commonly available in three commercial forms. First, as a water-dispersible solid, polyacrylamides may be used in applications such as hydro-seeding and canal sealing. This form slowly dissolves in water, but has a tendency to agglomerate when added too quickly or all-at-once to water. When this happens, the lumps that are formed take hours, days or even weeks to dissolve in water. This slow dissolution property is advantageous in some applications, but is a highly undesirable trait in situations that require quick dispersion of the polymer.

Second, water-dispersed polymers are used that have the distinct advantage of already being dissolved. Examples of water-dispersed polymers may be found in agricultural spray deposition aids, among others. However, not much polymer can be dissolved in water—only about two percent (2%), before the solution becomes too viscous to be handled easily.

Traditionally, the third historical form is a water-in-oil (W/O) emulsion. This involves utilizing a polyacrylamide where the polyacrylamide chains are contained in small droplets of water that are dispersed in oil by using emulsifiers to help make the two phases mix. Emulsions are droplets or "bubbles" of liquid, known to those practiced in the art as "micelles," suspended in another liquid with which the first liquid will not mix. The micelles are often called the "discontinuous phase" and the suspending liquid is called the "continuous phase."

In the case of polyacrylamide emulsions, the polyacrylamide polymer is dissolved in the discontinuous phase, in this case, the water phase, while the continuous phase is oil. This is known as a water-in-oil (W/O) emulsion or a reverse emulsion. This type of emulsion keeps the polymer in small packets of water, which burst open when the emulsion comes into contact with water. Polyacrylamide-based W/O emulsions disperse well in water with vigorous stirring, and are used prevalently in water treatment.

Such emulsions are also used, among other things, in pesticide tank mixtures to aid in preventing drift and increasing deposition on target species. The problems with W/O emulsions are that they form solid lumps and other forms when the emulsion is added to water with little or no agitation or if the water-to-emulsion ratio is too low. Also, emulsions are inherently unstable and will eventually break or separate into oil and water layers. The oil rises as a layer, and the water layer sinks. Since the polymer chains are now free to combine, because they are not separated by the oil "walls" (that is the oil and water separation or dividing line), they combine to form large lumps.

The polyacrylamide polymer itself comes in several types, defined by electrical charge of the polymer chain. The polyacrylamide polymer may be nonionic, anionic or cationic. The cationic form is commonly used in water treatment. In the agricultural applications, the cationic, or positively charged polymer, is rarely used, as it has a deleterious effect on aquatic wildlife. The nonionic or uncharged form is a reaction product of pure acrylamide, forming an uncharged, but water-soluble polymer that is quite inert in the environment.

Acrylamide is co-reacted with other monomers to form the cationic or anionic forms. To form the anionic polymer, acrylamide is most often reacted with an acrylate monomer that is further reacted so that it becomes negatively charged. The nonionic and anionic polymers have different properties. At lower levels in water, the anionic polymers build properties, such as viscosity, faster. Anionic polyacrylamide polymers are compatible with other charged molecules, such as are contained in fertilizers. However, they can react undesirably with certain other charged molecules. Thus, nonionic polyacrylamides are used in situations where the anionics are incompatible with other molecules.

The amount of charge is measured as a percent of the comonomer added. Thus, a polyacrylamide that is 30% acrylate and 70% acrylamide is called a 30 percent-charged polymer. This percentage may be expressed as weight or mole percent, depending on the manufacturer. Typically, if the polymer is a combination of the two monomers, the acrylic acid portion is reacted with base to form the acid salt. The polymer is then considered to be charged.

Microemulsions are a very recent, commercially available development. A microemulsion is a special type of emulsion that has the same basic structure as traditional emulsions, except that the droplets are smaller. Smaller droplets, by virtue of the solution physics involved, are very stable and the droplets do not combine or separate in solutions as traditional emulsions do. Microemulsions are also virtually clear, while sometimes having only a slight haze, as opposed to standard emulsions which are typically milky white.

Polyacrylamide microemulsions have their own disadvantages, however. The prevalent disadvantage of a polyacrylamide microemulsion is that if it is combined with water or aqueous solutions, the polyacrylamide microemulsion will tend to form a skin at the surface that drastically reduces water diffusion, such as the diffusion of oil and/or emulsifier combination into the water phase. This is due to the fact that there are very many small aqueous droplets near the surface of the emulsion. When the small aqueous droplets are combined with water, water diffuses quickly across the discontinuous phase and swells the micelles nearest the surface. The micelles swell, combine, burst and rupture, in that order.

This almost instantaneous bursting of many of the droplets entangles the polymer on the surface of the microemulsion and forms a barrier, which, in turn, slows diffusion of water further into the microemulsion and dispersion of the rest of the polymer. This phenomenon, sometimes known as "skin" or "skinning," causes the same problems that traditional emulsions have in terms of dispersion and clean out.

Observers of microemulsions may actually observe that they are clear and therefore question the ability of the product to do the job intended or observe the presence, in this case, of polymer until the product is added to water, which causes the characteristic milky appearance and slimy feel of polyacrylamide emulsion added to water appear.

While each of the polymers and the delivery systems has distinct advantages, certain applications create great disadvantages for all polymers. For example, in agricultural fields that are watered using pivot irrigation, the polymer polyacrylamide is known to have been tested and shown to be effective at reducing the need for water. However, handling of the traditional emulsion, which is, thus far, the only economical form for this application, can plug pumps, nozzles, screens, or other apparatus, when the tedious clean out procedures necessary following application and if not done properly can lead to the lumping process described above. Microemulsions have been tested in this process and have been found to have the same problems because of the skinning described above.

Moreover, as noted, polyacrylamide requires surfactant and/or emulsions systems useful for admixing the polyacrylamide to form stable microemulsions. Specifically, a surfactant or emulsion system should be useful to effectively stabilize the aqueous discontinuous phase in oil to prevent phase separation and other like problems. The present invention provides emulsifier systems for stabilizing polyacrylamide-containing microemulsions.

Water repellant soils may cause serious issues when attempting to enhance the ability of plants to uptake water and other materials, such as fertilizers and/or pesticides. Specifically, water-repellant soils typically retard water infiltration into the soil matrix rendering the soil impervious to water penetration leading to underutilized application or misapplication moving away from the target area. Runoff of applications of fertilizers and/or pesticides, as well as soil erosion may result, especially during heavy rainfalls and/or irrigation conditions, causing fertilizers and/or pesticides to flow into water systems, such as reservoirs, lakes and rivers. Surfactants may be utilized to allow water infiltration of water-repellant soils, but many surfactants tend to burn plants or cause other like damage to plants, such as agricultural products, growing in the water-repellant soils.

Another form of water-repellant soil is so-called "crusted" soils, such as soils that have high amounts of organic matter built up on or near the surface of the soils. The crust may act as a barrier for the penetration of water, especially aqueous systems, which would be useful for providing water, fertilizers and/or pesticides to the root systems of plants.

Because it may be difficult to deliver pesticides and/or fertilizers to roots through water-repellant soils, known methods of delivering materials, such as pesticides specifically, may include boring into trees or other vegetation to deliver the useful materials. Of course, boring causes damage to trees and other vegetation, thereby weakening the trees or other vegetation.

It is generally known that ethylene oxide/propylene oxide (EO/PO) block copolymer has useful properties for wetting soils, for example, especially when used in agricultural, turf, ornamental or other compositions, especially on water repellant soils. However, EO/PO is notoriously difficult to mix into oil-containing systems.

EO/PO block copolymer has heretofore not been combined with W/O emulsions of polyacrylamide to obtain the useful properties of both the polyacrylamide (water retention) and the EO/PO block copolymers (water penetration). This is so because one would not expect EO/PO block copolymer to be useful in mixing in such a system because of its inherent incompatibility with oils. An EO/PO block copolymer is a long chain polymer made with ethylene oxide and propylene oxide portions. Thus, one would not expect EO/PO to mix well in W/O emulsions, especially due to the fact that EO/PO block copolymer hydrophobic portion, the PO block portion, is not a good lipophile or oil-loving molecule. Since, typically, emulsifiers (molecules that contain both water-loving and oil-loving portions) must contain a strong lipophile to be an effective ingredient in an emulsions or microemulsion, one of ordinary skill in the art would not look to include EO/PO block copolymer in a W/O emulsion, especially in combination with the polyacrylamide.

SUMMARY

A first aspect of the present invention provides a water-in-oil microemulsion, including a polyacrylamide, a fatty acid, a surfactant, an oil continuous phase, and an aqueous discontinuous phase in the oil continuous phase. The fatty acid includes a tall oil fatty acid, oleic acid, or a combination of a tall oil fatty acid and oleic acid. The water-in-oil microemulsion contains 6 to 48 parts by weight of the polyacrylamide, 30 to 62 parts by weight of the fatty acid, and 20 to 44 parts by weight of the surfactant per 100 parts by weight of the polyacrylamide, the fatty acid, and the surfactant combined.

According to a second aspect of the present invention, a method of dispersing a water-in-oil microemulsion into an aqueous medium and applying the water-in-oil microemulsion dispersed in the aqueous medium in an agricultural application is provided. The water-in-oil microemulsion includes a polyacrylamide, a fatty acid including a tall oil fatty acid and/or oleic acid, a surfactant, and an oil continuous phase, an oil continuous phase, and an aqueous discontinuous phase in the oil continuous phase, wherein the water-in-oil microemulsion contains 6 to 48 parts by weight of the polyacrylamide, 30 to 62 parts by weight of the fatty acid, and 20 to 44 parts by weight of the surfactant per 100 parts by weight of the polyacrylamide, the fatty acid, and the surfactant combined. Micelles of the water-in-oil microemulsion are allowed to burst in the aqueous medium. The aqueous medium with the water-in-oil microemulsion dispersed therein is applied to at least one seed, at least one growing crop, at least one forest area, at least one turf or other vegetation, at least one soil, at least one crop, or a combination thereof.

A third aspect of the present invention provides a method of dispersing a water-in-oil microemulsion into an aqueous medium and applying the water-in-oil microemulsion dispersed in the aqueous medium. The water-in-oil microemulsion includes a polyacrylamide, a fatty acid including a tall oil fatty acid and/or oleic acid, a surfactant, and an oil continuous phase, an oil continuous phase, and an aqueous discontinuous phase in the oil continuous phase, wherein the water-in-oil microemulsion contains 6 to 48 parts by weight of the polyacrylamide, 30 to 62 parts by weight of the fatty acid, and 20 to 44 parts by weight of the surfactant per 100 parts by weight of the polyacrylamide, the fatty acid, and the surfactant combined. Micelles of the water-in-oil microemulsion are allowed to burst in the aqueous medium. The aqueous medium with the water-in-oil microemulsion dispersed therein is applied to at least patch of bare ground, at least one roadside, at least one industrial area, at least one right-of-way, at least one water management area, at least one waterway, or a combination thereof.

According to a fourth aspect of the invention, a method of making a water-in-oil microemulsion is provided. The method involves combining a nanoemulsion of a polyacrylamide with a fatty acid including a tall oil fatty acid and/or oleic acid, a surfactant, and an oil continuous phase to form a microemulsion comprising an oil continuous phase and an aqueous discontinuous phase in the oil continuous phase, wherein the water-in-oil microemulsion contains 6 to 48 parts by weight of the polyacrylamide, 30 to 62 parts by weight of the fatty acid, and 20 to 44 parts by weight of the surfactant per 100 parts by weight of the polyacrylamide, the fatty acid, and the surfactant combined.

Other aspects of the invention, including apparatus, devices, systems, processes, and the like which constitute part of the invention, will become more apparent upon reading the following detailed description of the exemplary embodiments.

BRIEF DESCRIPTION OF THE SEVERAL VIEWS OF THE DRAWING(S)

Figure 2:
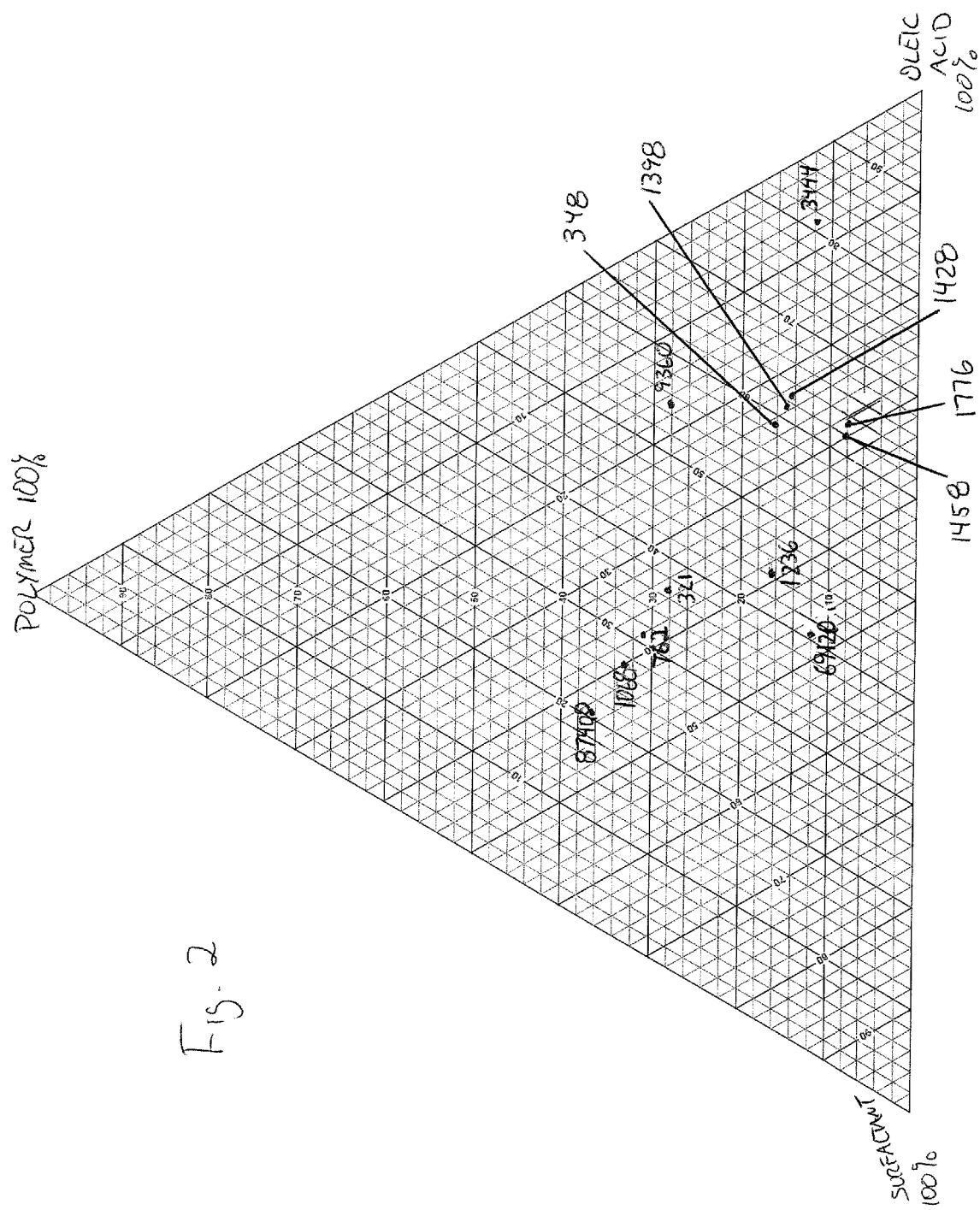

The accompanying drawings are incorporated in and constitute a part of the specification. The drawings, together with the general description given above and the detailed description of the exemplary embodiments and methods given below, serve to explain the principles of the invention. The objects and advantages of the invention will become apparent from a study of the following specification when viewed in light of the accompanying drawings, wherein:

FIG. 1 is an equilateral triangular graph of results of examples reported herein; and FIG. 2 is another equilateral triangular graph of results of further examples reported herein.

DETAILED DESCRIPTION OF THE EXEMPLARY EMBODIMENTS AND EMBODIED METHODS OF THE INVENTION

In accordance with exemplary embodiments described herein, there is provided a water-in-oil microemulsion including a polyacrylamide, a fatty acid, a surfactant, an oil continuous phase, and an aqueous discontinuous phase in the oil continuous phase. The microemulsion may contain other components, such as, by way of example, pesticides and/or fertilizers, that may be delivered to trees, plants or other vegetation. For the purpose of this disclosure, "pbw" means parts by weight.

Polyacrylamide

The present invention comprises an effective amount of polyacrylamide copolymer in a W/O microemulsion or nanoemulsion to impart desired characteristics, especially when combined with an aqueous medium, such as water, for use thereof. Specifically, the polyacrylamide may be desired to hold and/or retain water.

Microemulsion compositions according to exemplary embodiments include an effective amount of polyacrylamide, generally in the form of a polyacrylamide microemulsion or nanoemulsion. The polyacrylamide is present in an amount of 6 to 48 pbw per 100 pbw of the polyacrylamide, the fatty acid, and the surfactant combined. In the content of the entire W/O microemulsion, the polyacrylamide may constitute, for example, up to about fifteen percent of the total weight of the W/O microemulsion. This content may then be further diluted in water at the time of use to impart the desired characteristics of the polymer to the water phase or to the material to which the water phase is applied, as described in more detail below. The range of polyacrylamide content may be about one percent (1%) to about ten percent (10%) by weight, more specifically about two percent (2%) to about eight percent (8%) by weight of the total weight of the W/O polyacrylamide. As should be apparent to one of ordinary skill in the art, the polyacrylamide microemulsion or nanoemulsion component may be any emulsion that imparts the effective amount of polyacrylamide solids, as described above. For example, a typical polyacrylamide emulsion useful for the present invention includes Kemira Superfloc brand polyacrylamide nanoemulsion having twenty two percent (22%) polyacrylamide copolymer solids content. However, any other polyacrylamide emulsion composition may be utilized as apparent to one of ordinary skill in the art to arrive at the desired polyacrylamide content.

The present invention requires less active ingredient of polyacrylamide content to allow bubbles to disperse in the water phase. Thus, as noted, it may be preferred for some applications for the composition to have no greater than about fifteen percent (15%) by weight polyacrylamide copolymer solids, because compositions having greater than about fifteen percent (15%) by weight polyacrylamide copolymer solids may be difficult to disperse in the aqueous phase. Thus, utilizing less polyacrylamide copolymer solids during manufacturing is a way to achieve this goal. A countervailing consideration is that more polyacrylamide copolymer solids imparts more of the desired property of water retention, thus higher amounts of polyacrylamide copolymer solids, such as higher than fifteen (15%) by weight, may be desired.

Anionic polyacrylamide is particularly useful in the present invention. The charge of the polyacrylamides may be from zero percent (0%) to about forty percent (40%) by weight, which may be resultant because the reaction forming the polyacrylamide generally starts with about zero percent (0%) to about forty percent (40%) by weight acrylic acid or acid salt. The polymer that may be formed with acrylic acid or an acid salt monomer is called anionic polyacrylamide because the polymer itself contains a negative charge, which is balanced by a cation, usually sodium. A polymer made with little or no acid or acid salt is considered nonionic polyacrylamide because the polymer essentially contains no charge. The range of charge disclosed herein is generally necessary to ensure compatibility of the polymer with the various types of ingredients in the tank mixes. Higher or lower charge may directly affect compatibility, as the higher charge may be generally more compatible with fertilizers, and the lower charge may be more compatible with other types of charged species that may form an insoluble salt with an anionic polymer.

The weight average molecular weight of the polyacrylamide may be up to about thirty-five megagrams (35 Mg) per mole. More preferably, the weight average molecular weight of the polymer may be up to about thirty megagrams (30 Mg) per mole. Most preferably, the weight average molecular weight of the polymer may be up to about twenty five megagrams (25 Mg) per mole. The range of concentrations disclosed herein may allow for the maximum flexibility in the use of the polymer. Ultra-high molecular weight polymers build viscosity quickly and are highly stable in soil. High viscosity and high stability are, generally, two desirable properties for the microemulsions disclosed herein.

Oil

The microemulsions of the exemplary embodiments are W/O emulsions. Any oil may be utilized that may be effective in forming the microemulsions, as described herein. The oil in the water-in-oil microemulsion may be methylated soybean oil ("MSO") or soy methyl ester ("SME"), or a paraffin oil, which may be utilized to form the stable microemulsion of polyacrylamide and EO/PO block copolymer. However, any effective oil may be used in an effective amount.

For example, oils that may be used to form the stable microemulsions may be: 1) petroleum oils, more preferably, paraffinic oils (e.g., white oils) and naphthalenic oils, and/or 2) naturally occurring oils such as seed oils, such as, cottonseed, canola, soybean, corn, palm kernel or coconut oil, and/or 3) derivatives of naturally occurring oils such as the methyl or ethyl esters or methylated or ethylated derivatives of the above-named oils.

A microemulsion having polyacrylamide may be formed utilizing, as starting materials, a polyacrylamide nanoemulsion and an amount of surfactant, such as an EO/PO copolymer (discussed below), that is combined with a methylated soybean oil or paraffin oil to form a W/O microemulsion.

The oils, taken singly or in mixtures as named, herein may constitute up to about ninety percent (90%) by weight of the composition. More preferably, the oils, taken singly or in mixtures as named, herein may constitute from about twenty (20%) to about eighty percent (80%) by weight of the composition. Most preferably, the oils, taken singly or in mixtures as named, herein may constitute about thirty percent (30%) to about seventy percent (70%) by weight of the composition.

Stabilizers

For the two phases of microemulsions to mix or "emulsify," a set of emulsifiers may be used. Generally, emulsifiers contain two areas or regions within the molecule, one that is hydrophobic and one that is hydrophilic. This structure therefore acts as "glue" that holds the two immiscible phases together, and interconnects the two phases together by going to the interface between the two phases and bridging the two, with the hydrophobic portion sticking into or otherwise contacting the oil phase and the hydrophilic portion sticking into or otherwise contacting the aqueous phase.

Exemplary embodiments described herein contain at least one fatty acid and at least one nonionic surfactant. This combination is unique in its ability to bring the two phases together and work together to stabilize the microemulsion. The one or more fatty acids and the one or more surfactants come together to form an easily water-dispersible microemulsion product with fewer handling issues. The terms "surfactant" and "emulsifier" may typically be used interchangeably, since all emulsifiers are surfactants and most surfactants are emulsifiers. These terms tend to differentiate the jobs each performs rather than any structural or chemical differences between them.

The presence of the fatty acids may be preferable in terms of dispersion as the fatty acids may act as the main contributor to slowing the diffusion of water and, therefore, bursting of the micelles into the water phase when dispersed in water.

This effective use of fatty acids is surprising, because it is known that ionic surfactants do not stabilize water-in-oil (W/O) emulsions well. The book "Chemistry and Technology of the Cosmetics and Toiletries Industry", D. F. Williams, W. H. Schmitt, Second Ed., Springer, 1996, p. 31, states, "A limited number of W/O emulsifiers are available. This is because ionic emulsifiers will not generally work in the case of W/O emulsions." Since fatty acids can form, and often are used as, negatively charged species, they are generally considered ionic emulsifiers.

The fatty acid may be one or more selected from the group consisting of $C_8$ to $C_{30}$ fatty acids. Such acids include, but are not limited to, myristic, lauric, palmitic, stearic, oleic, and linoleic acids and mixtures of fatty acids derived from natural sources such as coco, lauryl, palm, soy, cottonseed and tall oil fatty acids. The fatty acid may include at least one fatty acid whose major content is $C_{18}$ fatty acids such as soy and tall oil fatty acids. An effective amount of fatty acid, as described herein, may be utilized. The fatty acid content may be, for example, up to about thirty percent (30%) by weight, about one percent (1%) to about twenty five percent (25%) by weight, or about five percent (5%) to about twenty percent (20%) by weight. The water-in-oil microemulsion may contain 6 to 48 parts by weight of the polyacrylamide, 30 to 62 parts by weight of the fatty acid, and 20 to 44 parts by weight of the surfactant per 100 parts by weight of the polyacrylamide, the fatty acid, and the surfactant combined.

In an exemplary embodiment, the fatty acid is a tall oil fatty acid, and the water-in-oil microemulsion contains 6 to 40 parts by weight of the polyacrylamide, 30 to 62 parts by weight of the tall oil fatty acid, and 20 to 44 parts by weight of the surfactant per 100 parts by weight of the polyacrylamide, the tall oil fatty acid, and the surfactant combined. In another exemplary embodiment using tall oil fatty acid, the water-in-oil microemulsion contains 8 to 32 parts by weight of the polyacrylamide, 30 to 60 parts by weight of the tall oil fatty acid, and 24 to 43 parts by weight of the surfactant per 100 parts by weight of the polyacrylamide, the tall oil fatty acid, and the surfactant combined.

In a further exemplary embodiment, the fatty acid is oleic acid, and the water-in-oil microemulsion contains 10 to 48 parts by weight of the polyacrylamide, 30 to 60 parts by weight of the oleic acid, and 20 to 39 parts by weight of the surfactant per 100 parts by weight of the polyacrylamide, the oleic acid, and the surfactant combined. In still a further exemplary embodiment using oleic acid, the water-in-oil microemulsion contains 16 to 32 parts by weight of the polyacrylamide, 30 to 60 parts by weight of the oleic acid, and 24 to 38 parts by weight of the surfactant per 100 parts by weight of the polyacrylamide, the oleic acid, and the surfactant combined.

Preferably, the nonionic surfactants include at least one surfactant selected from the group consisting of ethoxylated surfactants, nonylphenol ethoxylates or alcohol ethoxylate or other ethoxylated surfactants. Better results may be obtained with nonylphenol ethoxylates or alcohol ethoxylate surfactants. The best results may be obtained with, most preferably, alcohol ethoxylates. The nonionic surfactant content may be up to about thirty percent (30%) by weight, or about one percent (1%) to about twenty five percent (25%) by weight, or about five percent (5%) to about twenty percent (20%) by weight based on the total weight of the microemulsion.

Another surprising property of the nonionic surfactant ingredient is the use of a nonionic surfactant or a combination of nonionic surfactants with a relatively high hydrophilic-lipophilic balance (HLB). HLB is the nature of a surfactant to have a balance between aqueous and nonaqueous phases. A low HLB surfactant has a high affinity for oily or nonaqueous phases and is generally highly insoluble in water. A high HLB value surfactant may generally have a high affinity for water and may form clear mixtures with water, even at high concentrations. Fatty acids generally have a long lipophilic chain terminated in a carboxylic acid moiety that is hydrophilic. The lipophilic portion generally dominates the molecule, however. Nonionic surfactant may generally have a carefully controlled HLB and range across the entire spectrum of HLB. Addition of the proper nonionic surfactant may allow the correct HLB value of the overall surfactant to be reached.

A nonionic surfactant or at least one nonionic surfactant in a combination of surfactants may have an HLB greater than 9.0, or about 9.0 to about 20, or about 9.3 to about 15. Nonionic surfactant and/or a combination of surfactant with at least one nonionic surfactant having a higher HLB are desirably used. By contrast, the fatty acids of the compositions may be very low HLB emulsifiers.

EO/PO Block Copolymer

The W/O microemulsion optionally may contain an EO/PO block copolymer. An amount of EO/PO block copolymer is optionally included in the compositions to impart improved water penetration, especially in hydrophobic media, such as in water repellant soils or crusted soils. Generally, an effective amount of EO/PO block copolymer may be up to about forty percent (40%) by weight, more preferably, about two percent (2%) to about thirty five percent (35%) by weight, most preferably about three percent (3%) to about thirty percent (30%) by weight.

The EO/PO block copolymer may include the straight block polymeric glycols obtained, for example, by the addition of ethylene oxide (EO) on a condensation product of propylene oxide (PO). Reverse block copolymers, which are also acceptable for use, may be prepared by reacting EO with itself to provide a hydrophile of designated molecular weight. PO is then added to obtain hydrophobic blocks on the outside of the molecule. Reversing the hydrophobic and hydrophilic blocks creates polymers that are similar to the regular EO/PO block copolymers, but with some important differences. While the EO/PO straight block copolymers tend to be better emulsifiers and dispersants and generally cover a broader range of molecular weights, the reverse block copolymers generally have lower foaming, greater defoaming, and reduced gelling tendencies.

The amount of polyacrylamide and optional EO/PO block copolymer utilized in an emulsion of the present invention may preferably be effective and economically viable. Delivering a solution that has too low polymer content may mean delivering too much water or other ineffective ingredient to a site, thereby causing shipping costs to be too high.

However, a polymer level that is too high may also be detrimental. It is well known to users that handle emulsions that adding a small amount of water to any emulsion may break the emulsion and cause it to gel. The gelling may cause a large, thick mass to form that does not dissolve easily in water and which may have to be stirred for days to dissolve completely. The lower level of polymer combined with the other elements/ingredients of the present invention may significantly reduce gelling.

Other Components

The microemulsions described herein may further include effective amounts of other components. Specifically, the present invention may act as a delivery system for effective amounts of components having a specific purpose, such as pesticides, such as insecticides, fungicides and other like pesticides, and/or fertilizers. For example, the compositions of the present invention may be useful for wetting and/or penetrating hydrophobic soils. Thus, the compositions of the present invention may be particular useful to deliver water and/or other components, such as pesticides and/or fertilizers to roots of vegetation through hydrophobic soils. Preferably, these other components may be admixed into the compositions of the present invention in their concentrated forms, prior to the addition of water. However, it should also be apparent to those of ordinary skill in the art that these other components may added after diluted with water and prior to delivery to a desired area or location, such as to hydrophobic soil.

The microemulsion may be achieved in at least two ways. A first way is to classically create the microemulsion using well-known techniques. These techniques are often employed in manufacturing microemulsions. However, the objective is almost always to create a microemulsion with the highest content of active ingredient possible. Thus, these microemulsions may classically be more than 15% polyacrylamide for economy of transport and value.

However, another way to create the microemulsion involves diluting the commercially available material with higher concentrations of oil and emulsifier. The commercially available microemulsion is relatively inexpensive compared to the cost of forcing a special reaction. Therefore, the "dilution method" of making a microemulsion is relatively simple and inexpensive, while effectively reaching the same objectives at less cost.

The benefits of certain exemplary embodiments of the present invention are at least two-fold. First, the microemulsions are more stable than normal emulsions, as is generally disclosed above. Thus, long-term storage may be possible and even likely, as opposed to other emulsions, which tend to have long-term storage problems. The second benefit involves the amount of polymers and the solutions in which they are delivered.

The exemplary embodiments and methods disclosed herein may address the problem of the formation of microemulsion "skin" by production of a dilute, but not too dilute, and stable microemulsion. This may be accomplished, in a practical and economic sense, through dilution of the microemulsion with oil. The addition of oil may create a thicker continuous layer through which water and water droplets must pass. This may slow diffusion of water from the bulk liquid into the droplets. The micelles, therefore, may swell more slowly. Slower dispersion of the droplets at the surface of the microemulsion and slower swelling of the droplets in the microemulsion may mean that the surface skin does not form when the microemulsion comes in contact with water.

However, addition of oil to the microemulsion alone may be inadequate. If oil is added directly to a typically manufactured polyacrylamide nanoemulsion, or any other emulsion for that matter, an unstable emulsion results and a discontinuous layer may separate from the continuous layer. The addition of further ingredients, typically more emulsifier, may be warranted to ensure a stable, easily-dispersed microemulsion having polyacrylamide content.

Exemplary embodiments disclosed herein may address the potential instability by addition of emulsifiers to form stable microemulsions. These emulsifiers balance the water and oil phases, and may be compatible with the emulsifiers that may be typically used in microemulsions. However, with the addition of more oil, the balance of the emulsifiers may be adjusted to coincide with the water/oil ratio change.

Of course, the ideal amounts of each component may depend on the amounts of the other components within the compositions. For example, the amount of fatty acids and/or surfactants needed to create stable microemulsions may vary depending on the ratio of oil to aqueous phase and also on the amount of polymer present in the aqueous phase. However, the fatty acid may not, typically, be used alone, i.e., without the surfactant. The fatty acid may preferably be balanced with one or more surfactants to ensure compatibility with the aqueous phase.

The addition of one or more supplementary nonionic surfactants may be desired, for example, to counteract or balance the possibility that the addition of fatty acid will throw off the balance between the hydrophilic and hydrophobic phases. Nonionic surfactants with a medium to high HLB, such as, for example, a nonionic surfactant having an HLB above about 9.3, are particularly useful.

The exemplary embodiments, and in particular the amount of oil, the amount and type of surfactant(s), the amount of polyacrylamide copolymer, and amount of fatty acid may be controlled to provide an economical, easy-to-handle solution. Exemplary embodiments disclosed herein may disperse substantially homogeneously in water, with substantially no "lumping" as that term is used in the art. The skinning, lumping and clumping that is a problem with other microemulsions and standard emulsions generally does not form. Yet, there is enough surfactant for the product to disperse into the water phase through a mechanism that releases the water droplets into the added water more slowly. Without being bound by theory, it is thought that the slower release may allow the polymers to disperse into the water to which it is added before other water droplets nearby in the microemulsion burst open or combine, thereby avoiding the entanglement that normally causes skinning or lumps.

Also, exemplary embodiments disclosed herein may be generally clearer, in terms of appearance, than other emulsions or microemulsions. In general, microemulsions typically have a slight haziness. They can be generally viewed through easily, but do have minor, but definitive, cloudiness. Exemplary embodiments disclosed herein may provide solutions that are crystal clear and stable.

The microemulsion of exemplary embodiments may disperse into the aqueous phase well because of the combination of oil and surfactants that surround the water droplets that may contain the polymer. If the amount and/or ratios of oil and surfactants are not correct, at least one of two things may occur.

First, if the mixture contains too much oil phase, the dispersion of polymer into the water may be slowed. Aside from this physical problem, there may also be financial consideration of utilizing too much oil phase. Microemulsions formed with too much oil phase will not, generally, have a viscosity issue, as the aqueous solutions of polyacrylamide typically do, but will become uneconomical for the same reason that the aqueous polymer solutions will be uneconomical. There will generally be too little polyacrylamide present to be effective, and, additionally, the solution surrounding the polymer will typically be more expensive than just plain water.

Second, if enough oil is not added or the oil/emulsifier ratio is too high in the amount of emulsifier or the emulsifier is too water soluble, the micelles will swell and burst too quickly, causing problems of skinning and lumping. After the stable microemulsion is produced, the product must be able to be utilized by diluting the product in water or water-based mixtures for application. The precise amounts of the various components of the compositions described herein may be determined by one of ordinary skill in the art without undue experimentation.

The ability to use exemplary embodiments disclosed herein properly is greatly enhanced over other solutions. The microemulsion may be added to any aqueous solution with a modicum of stirring or movement. It will disperse well, not forming lumps or clumps. The means of addition may be in the form of pouring, as into a container or tank, or by injection, as into a pipeline using a pump and check valve, or by any other means of addition apparent to one of ordinary skill in the art where the microemulsion is dispersed into an aqueous liquid.

In another embodiment, compositions embodied herein may be spray treated onto dry carriers that may then be stored for extended periods of time. In addition, spray treating onto a dry carrier may enhance the ease of handling the compositions. When desired for use, the dry carrier having the compositions of the present invention spray treated thereon may be combined with water to form a dispersion for application thereof.

There are multiple uses for the exemplary embodiments disclosed herein. In use, the compositions may be used, for example, by dispersing the microemulsion in an aqueous media when ready for use. Exemplary uses are described below.

One use is in irrigation. Dispersions (or solutions) of the microemulsion may be pumped, using an injection pump or piston or other design, into a pipe carrying irrigation water to a pivot or other delivery system. Because of the superior dispersion properties of exemplary embodiments described herein, there is no need to further treat or add other ingredients. The injection is followed directly by a water rinse. The water rinse may easily move through the pump without complications.

Another use is in an agricultural or non-agricultural spray tank mix containing pesticides. Solutions of the microemulsion may be added directly into the tank while the ingredients in the tank are being stirred. Again, the dispersion is generally very easy, not forming lumps or clumps in accordance with exemplary embodiments disclosed herein.

Solutions of the microemulsion may also be used in pesticide tank mixes for several reasons. First, the solutions may provide the ability to control the deposition of a pesticide to a target species. The presence of a deposition aid or drift control product may generally be required in the future to control drift in order to reduce drift of pesticides onto non-target species.

The exemplary compositions disclosed herein may be added into an aqueous medium to impart the desired properties. The aqueous medium may then be used in a desired fashion. Such uses may include, but are not limited to, applying the microemulsion to at least one seed, at least one growing crop, at least one patch of bare ground, at least one roadside, at least one industrial area, at least one soil erosion area, at least one right-of-way, at least one forest area, at least one turf or other vegetation, at least one soil, at least waterway, at least one crop, at least one fertilizer, at least one water management area or various combinations thereof.

In addition, the polyacrylamide microemulsion in a W/O dispersion, particularly when the EO/PO block copolymer is included, may be particularly useful in applications whereby wetting is required. For example, in soils having poor wettability, the compositions disclosed herein may be particularly useful for wetting of poorly wettable soils. Moreover, the compositions may be useful for imparting anti-crusting properties, such as helping to prevent the buildup of organic material that may crust and otherwise create a barrier to water penetration.

Forming the aqueous dispersions of the present invention may be accomplished in any suitable fashion. Typical forming processes may include, but are not limited to, forcing the composition into the aqueous medium by at least one operation selected from the group consisting of stifling the aqueous medium and the composition, pumping the aqueous medium and the composition through a pipe or stifling it in a tank, pouring the composition into a tank containing the aqueous media and injecting the composition into the tank.

The following non-limiting examples are intended to illustrate the present invention without unduly limiting the scope of the present invention.

EXAMPLES

The microemulsions of the exemplary embodiments are easily pumped using standard piston, check valve and other pumps because the microemulsion remains fluid and well below the maximum viscosity of the pumps used in agricultural and irrigation applications. That maximum viscosity is about 1000 cps. In fact, emulsions and microemulsions are used because they can deliver large amounts of polymer in a concentrated form to the injection site at low viscosities.

However, when the pump needs to be cleaned out, for example, in order to deliver the next product, such as fertilizer, the pump generally must be cleaned out with some fluid that is readily available, inexpensive, and preferably environmentally safe. The preferred cleanout fluid is water, which is readily available at well-heads. Experience has shown that with standard emulsions and previous micro- and nanoemulsions that cleaning the pump with water causes the pump to plug. This is because the mixing interface between the emulsion and the water goes through a viscosity curve as the water and emulsion mix. The external water diffuses to the water micelles, causing them to swell, combine and burst. As the water micelles swell and combine, the viscosity increases and the polymer molecules, once separated by the oil continuous phase, entangle. This entanglement, on a large scale, causes a dramatic increase in viscosity. As an example of the sorts of viscosities that can be achieved, there are commercial products that, when combined with water a rate of 1-2% pure polymer, reach 2000 cps or more. At higher levels, the polymer becomes too thick to pour out of a bottle because the solution can reach 4500 cps. The more polymer that is added, the higher the viscosity.

So, when the polymer is mixed with water in the pump, it goes through a transition where the amount of polymer starts out at its maximum level and decreases as water diffuses in the system. However, the swelling, combining and bursting on a large scale can cause polymer levels that far exceed that 1-2% level that make the polymer solution pumpable and far exceed the ability of a pump that is capable of pumping a solution at about 1000 cps to be able to pump. While one can imagine that a microemulsion polymer may contain 2, 4, 8, 16 or 20% or more polymer, the local water diffusion would cause local polymer levels at the interface to reach much higher levels when the oil phase is displaced. This causes the dramatic viscosity increase that can make the polymer unpumpable.

As water diffuses and the material becomes thicker, water diffusion slows dramatically because physical mixing cannot be achieved in the pump. Only when the amount of water sufficiently dilutes, and therefore begins to untangle the polymer, does the viscosity begin to decrease. This cause a viscosity curve at which some maximum is reached at a certain percentage of water less than 100% but greater than zero. If the maximum viscosity achieved is lower than the pump can handle, the pump will continue to pump the fluid. If the viscosity of the mixed water and microemulsion goes above the pump's maximum viscosity, the fluid will stop moving and the pump will be plugged.

A system that would slow down diffusion of the water to the micelles or reduce swelling, combining and bursting would reduce the level of viscosity achieved at the interface. Any test that can test the maximum viscosity achieved during the mixing of the water and microemulsion would give an indication of the maximum viscosity that could be experienced by a system.

In order to mimic the diffusion and mixing, water was combined at various levels to determine the viscosity curve of the microemulsion. Three formulation variables were tested in order to examine the effect of those variables vis-à-vis the maximum viscosity. These variables were percent nonionic surfactant, percent fatty acid, and percent polymer. These materials were mixed in various ratios. Various combinations of these three materials were mixed and observed for clarity, an indication of stability. The clearer the mixture is, the more stable it will be. A completely clear mixture may be stable for years, a commercially desirable feature.

After the combinations were prepared, each was tested for viscosity by the following procedure. 100 g of total solution was used in order to test the viscosity. Water was added to the prepared solution. The ratio of water and prepared solution were varied by adding 10, 20, 30, 40 and 50% by weight water to the prepared polymer microemulsion. Fresh microemulsion was used with each combination of water and microemulsion. In other words, separate samples that were 10% water and 90% microemulsion, 20% water and 80% microemulsion and so on, were prepared. Immediately after the water and microemulsion were combined, the mixture was stirred for 1 minute using an overhead stirrer. After stirring, the water/microemulsion mixture was immediately moved to a viscometer. The viscometer was a Brookfield LVDV-1+ dynamic digital viscometer. The viscometer was started and allowed to spin for one minute, after which the reading was taken. The viscometer, being digital, provides the reading directly in centipoise.

The data has four independent variables, i.e., the percentage of each of the three components and the percentage of water added for viscosity testing, and one dependent variable, i.e., the viscosity measured. However, only the maximum viscosity needs to be reported for each water/microemulsion combination. This is because, as stated above, if the viscosity remains less than 1000 cps at all water percentages, then the mixture remains pumpable. If the viscosity of the water/microemulsion mixture goes over 1000 cps at any combination, then diffusion, rather than mixing, becomes limiting and plugs the pump. Therefore, the maximum viscosity achieved is the determining factor for whether a mixture will plug a pump or not.

Examples 1-13

Examples 1-13 contained a blend of E-4366 microemulsion (Kemira), tall oil fatty acid, and Tergitol NP9.5 surfactant (Dow Chemical). Oil was added in an equal weight amount to bring the added oil content to 50 weight percent. The percent by weight for each component was determined, taking into consideration the presence of additional surfactant present in the Kemira product. The blends, weight percentages and measured viscosities are reported below in Table 1. The viscosities are reported in a triangular graph form in FIG. 1, which allows the reporting of four-dimensional data in two dimensions. Each side of the triangle represents a respective one of the three dependent variables—i.e., the percentage of nonionic surfactant, fatty acid and polymer. The numbers plotted on the graph are the maximum viscosity achieved for that mixture.

TABLE 1

| EX. | Blend | Polyacrylamide (%) | TOFA (%) | Surfactant (%) | Viscosity (cps) |
|---|---|---|---|---|---|
| 1 | 80/10/10 | 36.4 | 20.7 | 42.9 | 58920 |
| 2 | 70/20/10 | 28.1 | 36.5 | 35.4 | 336 |
| 3 | 70/30/0 | 28.1 | 54.9 | 17.0 | 3120 |
| 4 | 50/30/20 | 16.2 | 44.4 | 39.4 | 978 |
| 5 | 50/40/10 | 16.2 | 59.1 | 24.7 | 276 |
| 6 | 40/30/30 | 11.9 | 40.4 | 47.7 | 7972 |
| 7 | 40/60/0 | 11.9 | 80.9 | 7.3 | 2424 |
| 8 | 30/40/30 | 8.2 | 49.6 | 42.2 | 642 |
| 9 | 0/90/10 | 0 | 90 | 10 | 26880 |
| 10 | 78/12/10 | 34.6 | 24.1 | 41.3 | 4548 |
| 11 | 76/14/10 | 32.8 | 27.5 | 20.2 (39.7%) | 1371 |
| 12 | 74/16/10 | 31.2 | 30.7 | 19.9 (38.1%) | 831 |
| 13 | 28/52/20 | 7.6 | 63.4 | 23.8 (29.0%) | 1002 |

Examples 14-26

Examples 14-26 contained a blend of E-4366 microemulsion (Kemira), oleic acid, and NP9.5 surfactant (Kemira). Oil was added in an equal weight amount to bring the added oil content to 50 weight percent. The percent by weight for each component was determined, taking into consideration the presence of additional surfactant present in the Kemira product. The blends, weight percentages and measured viscosities are reported below in Table 2. The viscosities are reported in a triangular graph form in FIG. 2, which allows the reporting of four-dimensional data in two dimensions. Each side of the triangle represents a respective one of the three dependent variables—i.e., the percentage of nonionic surfactant, fatty acid and polymer. The numbers plotted on the graph are the maximum viscosity achieved for that mixture.

TABLE 2

| EX. | Blend | Polyacrylamide (%) | Oleic Acid (%) | Surfactant (%) | Viscosity (cps) |
|---|---|---|---|---|---|
| 14 | 80/10/10 | 36.4 | 20.7 | 42.9 | 87400 |
| 15 | 70/20/10 | 28.1 | 36.5 | 35.4 | 321 |
| 16 | 70/30/0 | 28.1 | 54.6 | 17.3 | 9360 |
| 17 | 50/30/20 | 16.3 | 44.3 | 39.4 | 1236 |
| 18 | 50/40/10 | 16.2 | 59.1 | 24.7 | 348 |
| 19 | 40/30/30 | 11.9 | 40.4 | 47.7 | 69120 |
| 20 | 40/60/0 | 11.9 | 80.8 | 7.3 | 3444 |
| 21 | 30/50/20 | 8.2 | 62.0 | 29.8 | 1458 |
| 22 | 76/14/10 | 32.8 | 27.5 | 39.7 | 1068 |
| 23 | 74/16/10 | 31.2 | 30.7 | 38.1 | 762 |
| 24 | 48/42/10 | 15.3 | 60.9 | 23.8 | 1398 |
| 25 | 46/44/10 | 14.4 | 62.6 | 23.0 | 1428 |
| 26 | 28/52/20 | 7.6 | 63.4 | 29.0 | 1776 |

The results show an unexpected viscosity minimum based with a combination of fatty acids and nonionic surfactant is achieved. In examples that provided viscosities of 1000 cps or less, pumps containing the emulsion may be cleaned via water flushing only. No special pre-rinse with out between the polymer injection and water cleanout is required, and special pumps are not needed for irrigation injection purposes, thus overcoming previous generations of gumming and clogging.

Example 27

The following ingredients were combined to form a microemulsion concentrate: paraffin oil—53% (Tolex RHT 70); polyacrylamide nanoemulsion—30% (Superfloc E 4366, 6.6% solids); tall oil fatty acid—10.2% (Mead Westvaco L5D); can be substituted with pine derived oleic acid; EO/PO reversed block copolymer—3.4% (Pluronic 10R5 (BASF)); nonylphenol ethoxylate—3.4% (NP 9.5). The above ingredients were added to a container in the order specified above. The mixture was stirred continuously while the ingredients were added. A crystal clear, golden mixture was formed.

Example 28

The following ingredients were combined to form a microemulsion concentrate: paraffin oil—34% (Tolex RHT 70); polyacrylamide nanoemulsion—40% (Superfloc E 4366, 8.8% solids); tall oil fatty acid—10.2% (Mead Westvaco L5D); can be substituted with pine derived oleic acid; EO/PO reversed block copolymer—3.4% (Pluronic 10R5 (BASF)); nonylphenol ethoxylate—3.4% (NP 9.5). The above ingredients were added to a container in the order specified above. The mixture was stirred continuously while the ingredients were added. A crystal clear, golden mixture was formed.

Example 29

The following ingredients were combined to form a microemulsion concentrate: methylated soybean oil (MSO)—80.91%; polyacrylamide nanoemulsion—9.87% (Superfloc E 4916, 2.17% solids); tall oil fatty acid—3.08% (Mead Westvaco L5D); can be substituted with pine derived oleic acid; nonylphenol ethoxylate—3.07% (NP6); EO/PO reversed block copolymer—3.07% (Pluronic L61 (BASF)). The above ingredients were added to a container in the order specified above. The mixture was stirred continuously while the ingredients were added. A crystal clear, golden mixture was formed.

Example 30

The following ingredients were combined to form a microemulsion concentrate: methylated soybean oil (MSO)—56.44%; polyacrylamide nanoemulsion—9.87% (Superfloc E 4916, 2.17% solids); tall oil fatty acid—1.85% (Mead Westvaco L5D); can be substituted with pine derived oleic acid; nonylphenol ethoxylate—1.84% (NP6); EO/PO reversed block copolymer—30% (Pluronic L61 (BASF)). The above ingredients were added to a container in the order specified above. The mixture was stirred continuously while the ingredients were added. A golden mixture with a very slight haze was formed.

Example 31

An amount of the composition of Example 30 (65.22%) was mixed with 34.78% Xytect 2F, an insecticide (Rainbow Treecare Scientific Advancements). A viscous white liquid was formed.

Example 32

An amount of the composition of Example 30 (1.25%) was mixed with 0.25% Xytect 2F, an insecticide (Rainbow Treecare Scientific Advancements) and 98.5% water. A hazy, uniform solution was formed.

Exemplary embodiments described herein may provide one or more of the following benefits: the delivery of polyacrylamide, a proven deposition aid or drift control agent, in a form that is stable for long periods of time; a polyacrylamide that mixes well in most tanks with EO/PO block copolymer for enhanced wetting properties of the composition; the composition that may be deliverable in one bottle; dispersability in water, including embodiments in which the maximum viscosity is not greater than 1000 cps; low aggregation; high stability and hence long shelf-life; enhanced handling characteristics; enhanced water-carrying properties; ability to treat soils, including water-repellant soils; superior wetting properties, particularly with EO/PO block copolymer present; and others described herein and determinable through practice of the exemplary embodiments.

The present invention as described herein, taken as a whole with the abstract, specification, and claims, provides sufficient information for a person of ordinary skill in the art to practice the invention disclosed and claimed herein. Any measures necessary to practice the present invention are well within the skill of a person having ordinary skill in the art after that person has made a careful study of the present disclosure.

Because of this disclosure and solely because of this disclosure, modification of these compositions and methods may become clearer to a person of ordinary skill in the art. Such modifications are clearly covered by the present disclosure.

It should be noted that various changes and modifications to the presently preferred embodiments described herein will be apparent to those skilled in the art. Such changes and modifications may be made without departing from the spirit and scope of the present invention and without diminishing its attendant advantages.

What is claimed is:

1. A method of dispersing a water-in-oil microemulsion into an aqueous media and applying the water-in-oil microemulsion in an agricultural application, comprising:

- dispersing a water-in-oil microemulsion in an aqueous medium, the water-in-oil microemulsion comprising
  - a polyacrylamide;
  - a fatty acid comprising a tall oil fatty acid, oleic acid, or a combination of a tall oil fatty acid and oleic acid;
  - a surfactant;
  - an oil continuous phase; and
  - an aqueous discontinuous phase in the oil continuous phase, wherein the water-in-oil microemulsion contains 6 to 48 parts by weight of the polyacrylamide, 30 to 62 parts by weight of the fatty acid, and 20 to 44 parts by weight of the surfactant per 100 parts by weight of the polyacrylamide, the fatty acid, and the surfactant combined;
- allowing micelles of the water-in-oil microemulsion to burst in the aqueous medium; and
- applying the aqueous medium with the water-in-oil microemulsion dispersed therein to at least one seed, at least one growing crop, at least one forest area, at least one turf or other vegetation, at least one soil, at least one crop, or a combination thereof.

2. The method of claim 1, wherein the fatty acid comprises the tall oil fatty acid, and wherein the water-in-oil microemulsion contains 6 to 40 parts by weight of the polyacrylamide per 100 parts by weight of the polyacrylamide, the tall oil fatty acid, and the surfactant combined.

3. The method of claim 1, wherein the fatty acid comprises the tall oil fatty acid, and wherein the water-in-oil microemulsion contains 8 to 32 parts by weight of the polyacrylamide, 30 to 60 parts by weight of the tall oil fatty acid, and 24 to 43 parts by weight of the surfactant per 100 parts by weight of the polyacrylamide, the tall oil fatty acid, and the surfactant combined.

4. The method of claim 1, wherein the fatty acid comprises the oleic acid, and wherein the water-in-oil microemulsion contains 10 to 48 parts by weight of the polyacrylamide, 30 to 60 parts by weight of the oleic acid, and 20 to 39 parts by weight of the surfactant per 100 parts by weight of the polyacrylamide, the oleic acid, and the surfactant combined.

5. The method of claim 1, wherein the fatty acid comprises the oleic acid, and wherein the water-in-oil microemulsion contains 16 to 32 parts by weight of the polyacrylamide, 30 to 60 parts by weight of the oleic acid, and 24 to 38 parts by weight of the surfactant per 100 parts by weight of the polyacrylamide, the oleic acid, and the surfactant combined.

6. The method of claim 1, wherein the water-in-oil microemulsion is homogenously dispersible in water or water-based mixtures to form a diluted product substantially completely free of solid agglomerates of the polyacrylamide.

7. The method of claim 1, further comprising an ethylene oxide/propylene oxide (EO/PO) block copolymer.

8. The method of claim 1, wherein the surfactant is nonionic and has a hydrophilic-lipophilic balance of greater than 9.3.

9. The method of claim 1, wherein the water-in-oil microemulsion has a total weight, and wherein the polyacrylamide constitutes up to about 15 percent by weight of the total weight.

10. The method of claim 1, wherein:

- the water-in-oil microemulsion has a total weight;
- the polyacrylamide constitutes up to about 15 percent by weight of the total weight;
- the fatty acid constitutes about 2 percent to about 5 percent by weight of the total weight; and
- the surfactant comprises a nonionic surfactant constituting about 9 to about 20 percent by weight of the total weight.

11. A method of dispersing a water-in-oil microemulsion into an aqueous medium and applying the water-in-oil microemulsion dispersed in the aqueous medium, comprising:

- dispersing a water-in-oil microemulsion in an aqueous medium, the water-in-oil microemulsion comprising
  - a polyacrylamide;
  - a fatty acid comprising a tall oil fatty acid, oleic acid, or a combination of a tall oil fatty acid and oleic acid;
  - a surfactant;
  - an oil continuous phase; and
  - an aqueous discontinuous phase in the oil continuous phase, wherein the water-in-oil microemulsion contains 6 to 48 parts by weight of the polyacrylamide, 30 to 62 parts by weight of the fatty acid, and 20 to 44 parts by weight of the surfactant per 100 parts by weight of the polyacrylamide, the fatty acid, and the surfactant combined;
- allowing micelles of the water-in-oil microemulsion to burst in the aqueous medium; and
- applying the aqueous medium with the water-in-oil microemulsion dispersed therein to at least one patch of bare ground, at least one roadside, at least one industrial area, at least one right-of-way, at least one water management area, at least one waterway, or a combination thereof.

12. The method of claim 11, wherein the fatty acid comprises the tall oil fatty acid, and wherein the water-in-oil microemulsion contains 6 to 40 parts by weight of the polyacrylamide per 100 parts by weight of the polyacrylamide, the tall oil fatty acid, and the surfactant combined.

13. The method of claim 11, wherein the fatty acid comprises the tall oil fatty acid, and wherein the water-in-oil microemulsion contains 8 to 32 parts by weight of the polyacrylamide, 30 to 60 parts by weight of the tall oil fatty acid, and 24 to 43 parts by weight of the surfactant per 100 parts by weight of the polyacrylamide, the tall oil fatty acid, and the surfactant combined.

14. The method of claim 11, wherein the fatty acid comprises the oleic acid, and wherein the water-in-oil microemulsion contains 10 to 48 parts by weight of the polyacrylamide, 30 to 60 parts by weight of the oleic acid, and 20 to 39 parts by weight of the surfactant per 100 parts by weight of the polyacrylamide, the oleic acid, and the surfactant combined.

15. The method of claim 11, wherein the fatty acid comprises the oleic acid, and wherein the water-in-oil microemulsion contains 16 to 32 parts by weight of the polyacrylamide, 30 to 60 parts by weight of the oleic acid, and 24 to 38 parts by weight of the surfactant per 100 parts by weight of the polyacrylamide, the oleic acid, and the surfactant combined.

16. The method of claim 11, wherein the water-in-oil microemulsion is homogenously dispersible in water or water-based mixtures to form a diluted product substantially completely free of solid agglomerates of the polyacrylamide.

17. The method of claim 11, further comprising an ethylene oxide/propylene oxide (EO/PO) block copolymer.

18. The method of claim 11, wherein the surfactant is nonionic and has a hydrophilic-lipophilic balance of greater than 9.3.

19. The method of claim 11, wherein the water-in-oil microemulsion has a total weight, and wherein the polyacrylamide constitutes up to about 15 percent by weight of the total weight.

20. The method of claim 11, wherein:
the water-in-oil microemulsion has a total weight;
the polyacrylamide constitutes up to about 15 percent by weight of the total weight;
the fatty acid constitutes about 2 percent to about 5 percent by weight of the total weight; and
the surfactant comprises a nonionic surfactant constituting about 9 to about 20 percent by weight of the total weight.

* * * * *